US00PP31113P2

(12) United States Plant Patent
Olesen et al.

(10) Patent No.: US PP31,113 P2
(45) Date of Patent: Nov. 26, 2019

(54) ***CLEMATIS* PLANT NAMED 'EVIPO081'**

(50) Latin Name: *Clematis viticella*
Varietal Denomination: Evipo081

(71) Applicants: Mogens Nyegaard Olesen, Fredensborg (DK); Raymond J. Evison, St Sampsons Vale (GB)

(72) Inventors: Mogens Nyegaard Olesen, Fredensborg (DK); Raymond J. Evison, St Sampsons Vale (GB)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/999,905

(22) Filed: Sep. 10, 2018

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./228
CPC ..... A01H 5/02; A01H 6/72
See application file for complete search history.

(56) References Cited

PUBLICATIONS www.poulsenroser.com/assortment/clematis-collections/boulevard/issey.aspx.2016.*

* cited by examiner

*Primary Examiner* — Annette H Para

(57) ABSTRACT

A new *Clematis* plant with a compact growth habit, profuse, red flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification:
Genus: *Clematis.*
Species: *viticella.*
Variety denomination: 'Evipo081'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2005 and the resulting seeds were planted the following winter in a controlled environment in Guernsey, Channel Islands, United Kingdom. The new variety named 'Evipo081' originated as a single seedling from the stated cross.

The new *Clematis* plant may be distinguished from its female seed parent and male pollen parent by the following characteristics. The female seed parent has a flower color of Red-Purple Group 60A while the new variety has Red Group 53A tepals. The male seed parent has deep pink tepals while the new variety has Red Group 53A tepals.

The objective of the hybridization of this *Clematis* plant was to create a new and distinct variety for nursery culture with unique qualities such as:

1. Uniform and abundant red flowers;
2. Vigorous and compact growth, making the variety suitable for container culture; and
3. Improved disease resistance.

This combination of qualities was lacking in *Clematis* plants that were in commercial cultivation and the qualities have been substantially achieved in the new variety.

'Evipo081' was selected by Mogens N. Olesen and Raymond J. Evison in their *Clematis* development program in the Channel Islands, United Kingdom in 2006. Asexual reproduction of 'Evipo081' by means of vegetative cuttings and traditional layering was first performed by Mogens N. Olesen and Raymond J. Evison in the nursery during the summer of 2006. This initial and subsequent asexual propagations have demonstrated that the characteristics of 'Evipo081' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo081'.

Specifically illustrated in FIG. 1 of the drawings shows an open flower, tepals detached, a flower bud upon opening, and reproductive flower parts.

DETAILED DESCRIPTION OF THE VARIETY

Figure 1:
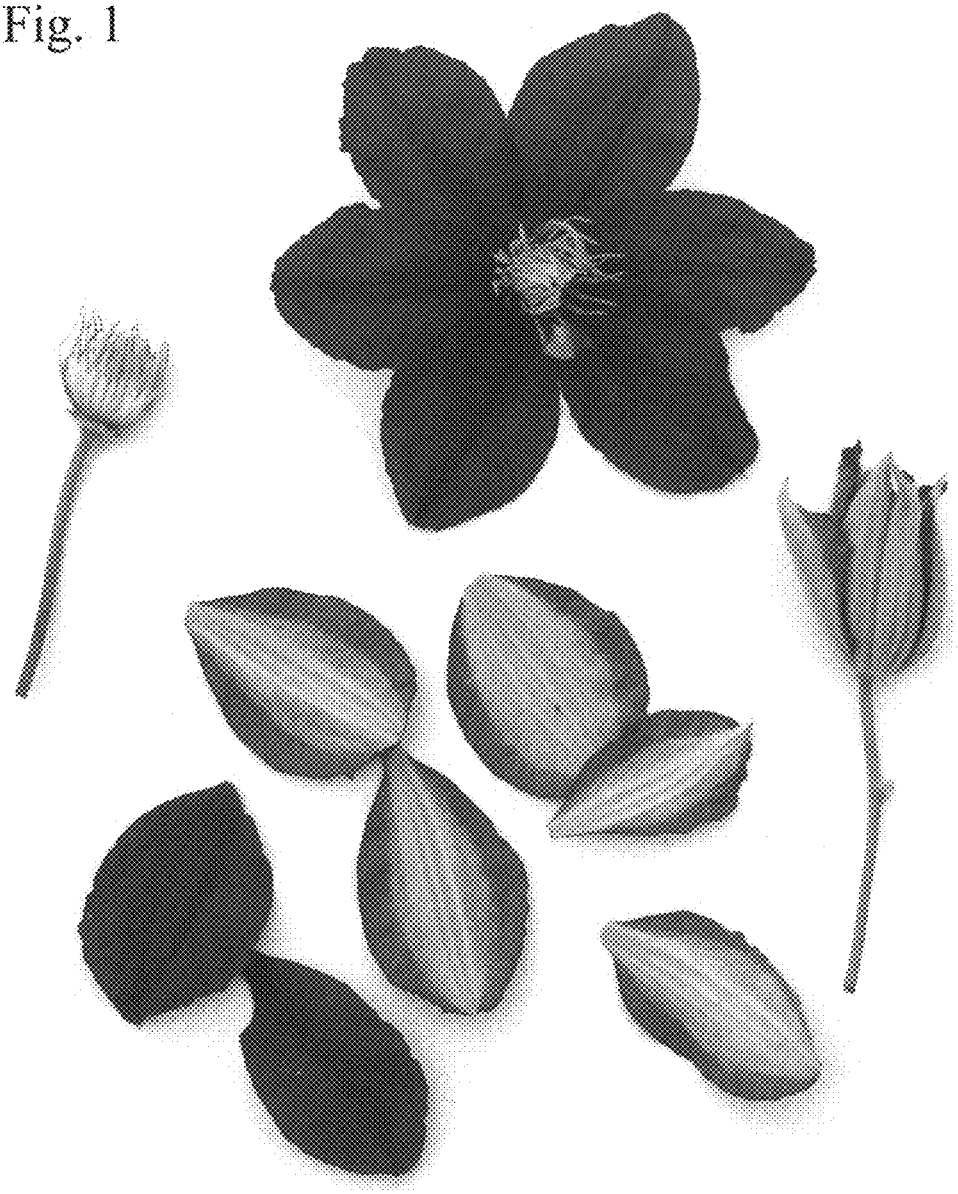
Figure 2:
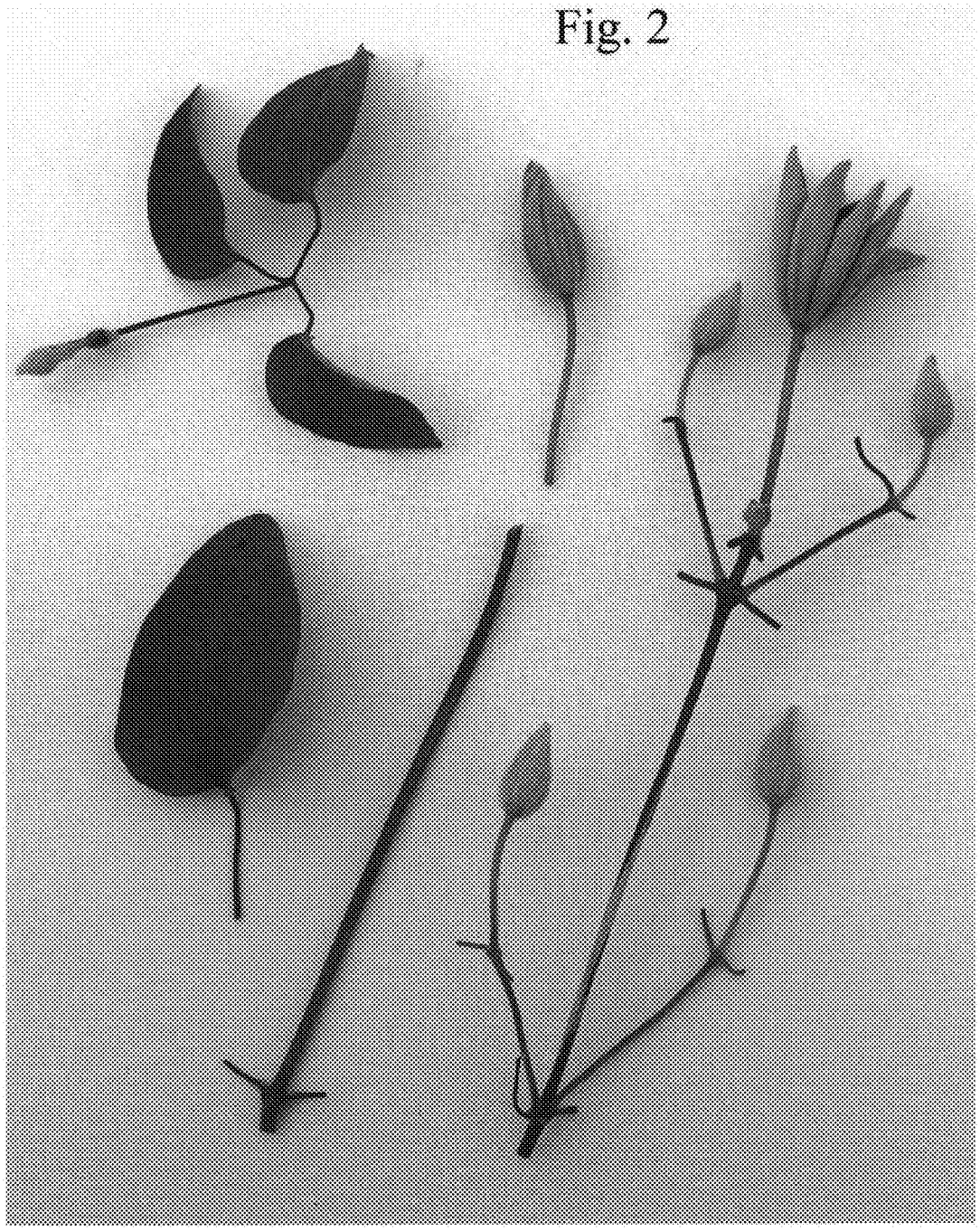
FIG. 2 shows leaves, stems, and flower buds attached to the stem. Illustrated plants are 2 years of age.

The following is a detailed description of 'Evipo081', as observed in its growth throughout the flowering period in Marion County Oreg. Observed plants were cultivated for a period of 24 months in open field. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *Clematis* variety 'Evipo016' described and illustrated in U.S. Plant Pat. No. 21,583 are compared to 'Evipo081' in Chart 1.

CHART 1

| | 'Evipo081' | 'Evipo016' |
|---|---|---|
| Flower diameter | 105 to 110 nun | 130-185 mm |
| Tepal upper surface | Red Group 53A | Red Group 53A |
| Tepal count | 6 | 6 |

FLOWER AND FLOWER BUD

Blooming habit: Continuous. The natural flowering period is generally from April to September.

Flower bud:

*Size*.—Normally 45 mm in length. Bud diameter is 16 mm.

*Bud form*.—Elliptic.

*Bud color*.—Yellow-Green Group 145C.

*Texture*.—Pubescent.

Pedicel:

*Surface texture*.—Smooth.

*Length*.—On average 30-40 mm in length with 3.5 mm diameter.

*Color*.—Yellow-Green Group 145C with intonations of Greyed-Orange Group 174A.

*Strength*.—Moderate.

Receptacle:

*Surface texture*.—Pubescent.

*Shape*.—Broad funnel.

*Size*.—2 mm (h)×4 mm (w).

*Color*.—Yellow-Green Group 145C.

Flower arrangement:

*Location on vine*.—New and old growth.

*Borne*.—Singly from terminal buds, and from axillary buds along the stem.

Flower bloom:

*Size*.—On average, flowers are 105 to 110 mm in diameter and 20 mm in depth.

*Profile*.—Open flowers are flat.

*Fragrance*.—None.

*Lasting quality*.—Flowers normally remain up to 10 days on the plant.

Tepals:

*Tepal color*.—The upper surface is Red Group 53A. The lower surface, has a central bar of Purple Group 76C and Yellow-Green Group 145B. The margins at the undersurface are Red-Purple Group 70B.

*Quantity*.—Normally 6 tepals.

*Size*.—About 55 mm in length by 31 mm wide.

*Shape*.—Individual tepal shape is broadly elliptic. The tepal apex is broadly acute. The tepal base is typically acute.

*Apex recurvature*.—None, slightly recurved.

*Tepal cross section*.—Flat.

*Margins*.—Entire. Moderate undulations of margin observed.

*Persistence*.—Tepals drop off cleanly.

Reproductive organs:

*Pollen*.—None observed.

*Anthers*.—Size: 8 mm in length. Color: Greyed-Yellow Group 160B. Quantity: On average, 38.

*Filaments*.—Color: Green-White Group 157B. Length: 7 mm.

*Pistils*.—Quantity: On average, 25.

*Stigmas*.—Inferior in location relative to the length of the filaments and the height of the anthers.

*Styles*.—Color: Green-White Group 157A. Length: About 11 mm.

Seed head characteristics: Seed not observed to date.

PLANT

Plant form: Climbing.

Plant growth: Compact.

Size: Seasons growth attains 60 cm in height. Average spread is 45 cm.

Stems:

*Color*.—Juvenile stems are Yellow-Green Group 144B. Mature stems are Greyed-Orange Group 177A.

*Internodes*.—On average, 65 mm between nodes.

*Length*.—Normally 15 cm from the base of the plant to the flowering portion of the stem.

*Diameter*.—About 3 mm.

*Texture*.—Mature stems are ribbed, slightly pubescent.

Plant foliage:

*Leaf characteristics*.—Deciduous.

*Arrangement*.—Ternate.

*Leaf size*.—Compound leaves are about 110 mm (l)×95 mm (w). Leaflets are about 40 mm (l)×33 mm (w).

*Abundance*.—On average leaves per 10 cm of stem.

*Leaf color*.—Juvenile upper Yellow-Green Group 144A. Juvenile lower Yellow-Green Group 144B. Mature upper Yellow-Green Group 147B. Mature lower Yellow-Green Group 147C.

*Stipules*.—Absent.

*Petioles*.—Size: Normally 50 mm in length by 2 mm diameter. Texture: Smooth. Color: Greyed-Orange Group 177A.

*Petioloule*.—Size: About 23 mm in length by 1.5 mm diameter. Texture: Smooth. Color: Greyed-Orange Group 177A.

*Leaflet shape*.—Elliptic. The base is rounded, apex acute.

*Margin*.—Entire.

*Surface*.—The upper side is smooth, the lower side is smooth.

*Thickness*.—Moderate.

*Glossiness*.—Moderately glossy.

Disease resistance: Subject to any disease that normally attacks the species. However the variety is more tolerant to *Clematis* wilt, *Ascochyta clematidina*, than some *Clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *Clematis* plant named 'Evipo081', substantially as described and illustrated , due to its abundant red flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *